United States Patent

Hirata et al.

Patent Number: 5,252,292
Date of Patent: Oct. 12, 1993

[54] AMMONIA SENSOR

[76] Inventors: Mitsutoshi Hirata, 2-8-8-206, Narashinodai; Ryutoku Yosomiya, 270-27, Maekaizuka-cho, both of Funabashi-shi, Chiba-ken; Soichiro Takenishi, 5-3-15, Nishiaraihoncho, Adachi-ku, Tokyo, all of Japan

[21] Appl. No.: 524,562

[22] Filed: May 17, 1990

[30] Foreign Application Priority Data

May 18, 1989 [JP] Japan ................................ 1-122943
Jul. 4, 1989 [JP] Japan ................................ 1-171168

[51] Int. Cl.⁵ .............................................. G01N 27/04
[52] U.S. Cl. .......................................... 422/98; 422/83; 422/90; 436/111; 436/113; 436/149; 204/400; 204/431
[58] Field of Search ........... 204/431, 400, 403, 298.02, 204/298.03; 252/500; 429/213; 436/113, 112, 111, 149; 422/98, 68.1, 83, 90

[56] References Cited

U.S. PATENT DOCUMENTS

| | | | |
|---|---|---|---|
| 4,297,173 | 10/1981 | Hikuma et al. | 436/113 X |
| 4,350,660 | 9/1982 | Robinson et al. | 422/90 |
| 4,662,996 | 5/1987 | Venkatasetty | 204/1 T |
| 4,822,465 | 4/1989 | Jones et al. | 204/192.1 |
| 4,839,020 | 6/1989 | Yamaguchi et al. | 204/431 |
| 4,886,572 | 12/1989 | Kimura et al. | 456/633 |
| 4,886,625 | 12/1989 | Albarella et al. | 252/500 |
| 4,904,553 | 2/1990 | Nakajima et al. | 429/213 |
| 4,984,446 | 1/1991 | Yagawara et al. | 73/31.06 |
| 4,997,541 | 3/1991 | Kiesele et al. | 204/402 |
| 5,057,436 | 10/1991 | Ball | 436/113 |

*Primary Examiner*—James C. Housel
*Assistant Examiner*—Long V. Le
*Attorney, Agent, or Firm*—Sherman and Shalloway

[57] ABSTRACT

An ammonia sensor consisting of at least one pair of electrodes and an ammonia-sensing material comprising a polyaniline filling the space between the electrodes.

13 Claims, 4 Drawing Sheets

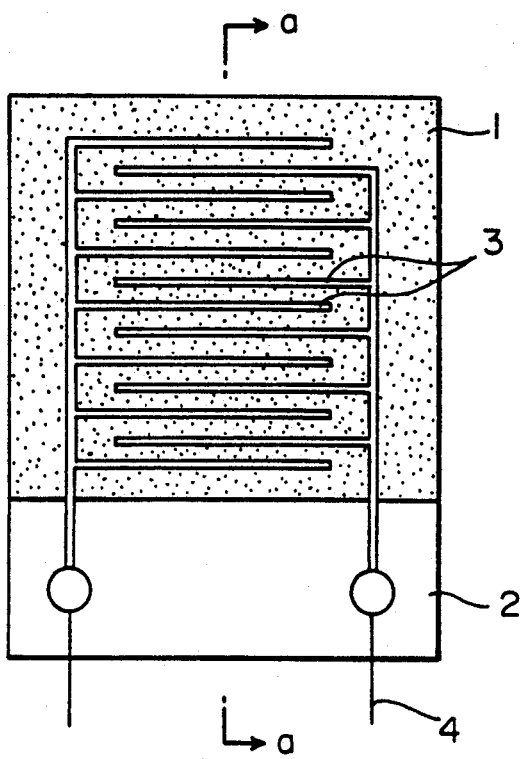
FIG. IA
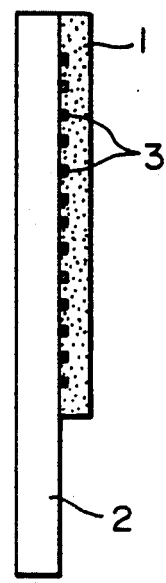
FIG. IB
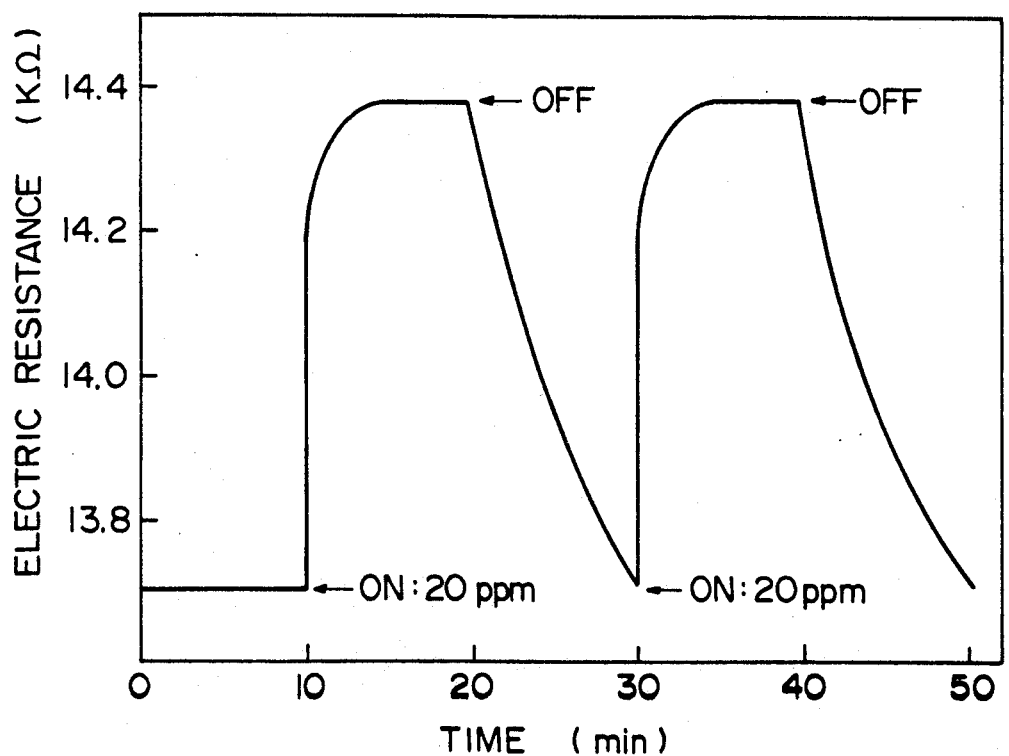
FIG. 2  OPERATING TEMP.: 30°C  RH: 50%

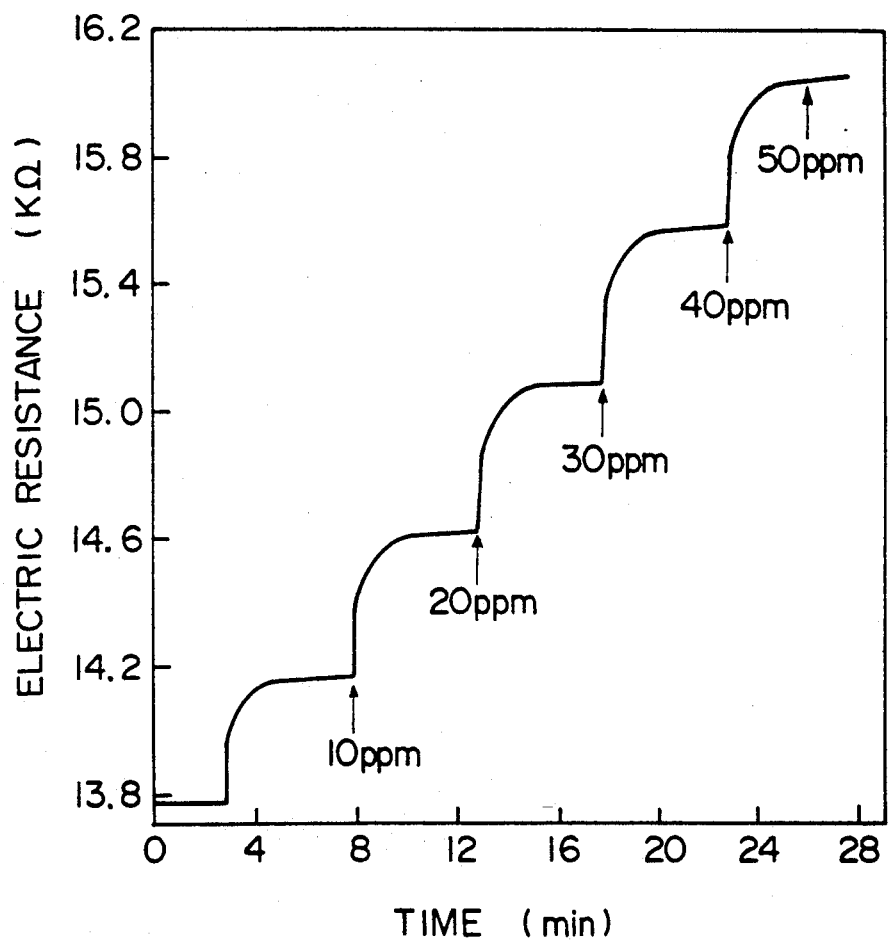

AMMONIA SENSOR

The present invention relates to an ammonia sensor and particularly to an ammonia sensor comprising a polyaniline as an ammonia-sensing portion.

As the sensor for ammonia gas detection, there were proposed, for example, (1) an ammonia gas electrode using an ammonia-permeable membrane, (2) a semiconductor sensor utilizing the change of resistance of an inorganic oxide semiconductor and (3) an ammonia detector using conductive polypyrrole. However, the ammonia gas electrode (1) is big in size, inconvenient to handle, impossible to use in a small space and troublesome in maintenance works such as make-up or exchange of electrolytic solution; the semiconductor sensor (2) generally has low selectivity for ammonia gas and must be used in a heated condition, and accordingly may cause explosion when used in an atmosphere wherein a flammable gas or a dust is present; the detector (3) using polypyrrole gives large property change with the lapse of a time. Thus, the conventional ammonia sensors have drawbacks.

Present inventors conducted a study in order to provide an ammonia sensor which is free from the above-mentioned drawbacks, is operable at room temperature, is small and lightweight, and has high reliability and high sensitivity. As a result, it was found that polyaniline changes its electric resistance in proportion to the ammonia concentration in a gas atmosphere such as air or other gas, that the utilization of this change in electric resistance enables the detection of ammonia concentration at a high sensitivity, and that polyaniline can be used very effectively as the sensing portion of an ammonia sensor. The finding has completed the present invention.

According to the present invention, there is provided as ammonia sensor consisting of at least one pair of electrodes and an ammonia-sensing material comprising a polyaniline filling the space between the electrodes.

The polyaniline used as an ammonia-sensing component in the ammonia-sensing material of the sensor of the present invention is a conductive organic polymer and can be produced by, for example, chemical or electrochemical polymerization of aniline [reference is made to, for example, A. G. MacDiarmid, J. C. Chiang and M. Halpern, Polym. Prepr. (1984) 248; B. Wang, J. Tang and F. Wang, J. Tang and F. Wang, Synthetic Metals, 13 (1986) 329-3341].

For example, the polyaniline can be produced by electrolytic polymerization of aniline wherein a polymerization solution containing aniline and an appropriate electrolyte is subjected to electrolysis in an ordinary electrolytic cell, using platinum as an anode and palladium as a cathode. In this case, the electrolytic voltage can be ordinarily 0.3-2 V (relative to a standard calomel-alumel electrode), and the current density is suitably 1-100 mA/cm$^2$. As the electrolyte usable in the polymerization solution, there can be mentioned, for example, mineral acids such as hydrochloric acid, sulfuric acid and the like; perchloric acids and their salts such as $HClO_4$, $NAClO_4$, $KClO_4$ and the like; phosphoric acid buffer tetraethylammonium fluoroborate; and organic sulfonic acids such as toluenesulfonic acid, naphthalenesulfonic acid and the like. The electrolyte can be used generally in a concentration of 0.01-5 M, preferably 0.03-4 M in the polymerization solution.

Aniline can be used in the polymerization solution generally in a concentration of 0.01-5 M, preferably 0.03-4 M. As the solvent usable in the polymerization solution, there can be mentioned, for example, water, ethanol, acetonitrile, propylene carbonate, nitrobenzene and their mixture.

The polyaniline formed by electrolysis can be separated from the polymerization solution, washed with water thoroughly until the washings become almost neutral, and dried until the residual water in polyaniline becomes 5% by weight or less, preferably 2% by weight or less.

The thus formed polyaniline is preferably soluble in ordinary polar organic solvents such as N,N'-dimethylformamide, N,N'-dimethylacetamide, dimethylsulfoxide, N-methylpyrrolidone, acetonitrile and the like.

The present inventors found that the polyaniline obtained by electrolytic polymerization as above changes its electric resistance in proportion to the ammonia concentration in an atmosphere such as air or other gas and accordingly the measurement of the electric resistance enables the detection of the ammonia concentration at a very high sensitivity and that the polyaniline is very effective as an element for ammonia sensor.

In using the thus obtained polyaniline as an ammonia sensor, the polyaniline can be dissolved in a polar organic solvent such as N,N'-dimethylformamide, N,N'-dimethylacetamide, dimethyl sulfoxide, N-methylpyrrolidone or the like, and the resulting solution can be coated on an insulating substrate having at least one pair of electrodes thereon, so as to fill the space between the electrodes. In a specific example, the polyaniline solution can be coated on an insulating substrate having a pair of interdigitated electrodes thereon as shown in FIG. 1, so as to fill the space between the electrodes and further cover the electrodes. The shape of electrodes has no particular restriction and can be not only a interdigitated-type Shape but also various other shapes such as whirl shape and sandwich shape in which a rectangular sensor membrane is sandwiched betwen electrode.

It is not necessary to add additives to the polymerization solution; however, as necessary, it is possible to add, for example, a polymer having film formability such as polyacrylonitrile, poly(vinyl chloride), poly(vinylidene chloride) or polystyrene, or a cellulose derivative, in such an amount as to give substantially no adverse effect on the ammonia-sensing ability of polyaniline.

The concentration of polyaniline in the polymerization solution is not particularly restricted but can be ordinarily 1-30%, preferably 3-20%. The electrodes is preferably made of a conductive metal with excellent corrosion resistance, such as platinum, gold, palladium or the like. As the insulating substrate, there is ordinarily used a ceramic such as glass, alumina or the like.

As the method for coating the polyaniline solution, there can be mentioned, for example, ordinary coating methods such as spin coating, dipping and the like. After the coating, the solvent is removed, whereby an ammonia sensor of the present invention can be obtained. The suitable film thickness after the solvent removal is generally 0.01-100 microns, preferably 0.1-10 microns.

It was found that in another process for producing an ammonia sensor according to the present invention, a thin film of a conductive high-molecular substance is formed on an insulating substrate having at least one pair of electrodes thereon, and then electrolytic polymerization of aniline is effected in the thin film with the thin film used as an anode, whereby an ammonia sensor comprising a polyaniline as an ammonia-sensing element can be produced very easily.

Therefore, according to another embodiment of the present invention, there is provided an ammonia sensor comprising at least one pair of electrodes and an ammonia-sensing material comprising a matrix of a conductive high polymer filling the space between the electrodes and a polyaniline dispersed in the matrix.

The conductive high polymer constituting the matrix of the ammonia-sensing material of the ammonia sensor can be any as long as it is a film-formable high polymer showing a conductivity of certain degree or higher (e.g. $10^{-5}$ mho or higher) when exposed to an electric field. The substance can have conductivity by itself, or can be a mixture with an electrolyte. Specific examples of such a conductive high polymer are as follows.

(a) High polymers having, as a side chain, an ionic group such as sulfonic acid group, carboxylic acid group, phosphoric acid group, secondary, tertiary or quaternary amino group or the like. For example, (co)polymers or graft polymers of an ionic group-containing monomer such as styrenesulfonic acid, acrylamide, methylpropanesulfonic acid, vinylsulfonic acid, acrylic acid, methacrylic acid, ethyleneimine, vinylpyridine or the like; carbamoyl cellulose, sulfated cellulose, etc.; high-molecular electrolytes obtained by chemically introducing an ionic group as mentioned above into an appropriate high-molecular substrate; and their crosslinked products.

(b) High polymers having conductivity by containing an electrolyte. For example, mixtures of a poly(alkelene oxide) [e.g. poly(ethylene oxide), poly(propylene oxide)] and an alkali metal salt; mixtures of an acrylonitrile type high polymer, a rhodanate and zinc chloride; salts between cellulose or its derivative and an alkali metal or an alkaline earth metal; high polymers each containing an anionic or cationic surfactant; mixtures of a water-soluble high polymer [e.g. polyvinylpyrrolidone, poly(vinyl alcohol)] and an alkali metal salt or an alkaline earth metal salt; high-moleculr substances each containing a dispersed amine. It is desirable that these high polymers, particularly those soluble in water be crosslinked by chemical or physical means after having been made into a thin film.

Of these conductive high polymers, there are preferably used in the present invention a high polymer having a sulfonic group or a carboxylic acid group as a side chain, its crosslinked product, a mixture of a poly(alkylene oxide) with an alkali metal salt, a mixture of an acrylonitrile type high polymer with a rhodanate and zinc chloride, and the like.

The ammonia sensor of the present invention can be formed, for example, by dissolving a conductive high polymer as mentioned above and a polyaniline produced as above, in a solvent capable of dissolving both of them and then coating the resulting solution on an insulating substrate having at least one pair of electrodes thereon, so as to fill at least the space between the electrodes. However, the ammonia sensor of the present invention can preferably be produced by forming a thin film of a conductive high polymer as mentioned above, on an insulating substrate having at least one pair of electrodes thereon, so as to cover at least the portion of the insulating substrate not covered by the electrodes and then effecting electrolysis of a polymerization solution containing aniline and an appropriate supporting electrolyte, in an electrolytic cell using the above-formed thin film of a conductive high polymer as an anode and platinum, palladium or the like as a cathode. As the insulating substance having at least one pair of electrodes thereon, there can be illustrated those mentioned above.

The formation of a thin film of a conductive high polymer on an insulating substrate having at least one pair of electrodes thereon can be effected by a per se known method, for example, a method wherein a solution of a conductive high polymer is prepared and then coated by, for example, spin coating, dipping, knife coating, roll coating or the like, a vapor deposition method (e.g. vacuum deposition), a plasma polymerization method or the like.

The suitable thickness of thin film of conductive high polymer can differ depending upon the type of the substance, etc. but is generally 0.1-100 microns, preferably 1-20 microns. The solution of the conductive high polymer can contain, as necessary, a film-formable polymer, etc.

The insulating substrate on which a thin film of a conductive high polymer has been formed, is placed in an electrolytic cell filled with a polymerization solution containing aniline and an appropriate supporting electrolyte; electrolytic polymerization of aniline is effected in the thin film of a conductive high polymer, using the thin film as an anode and palladium or the like as a cathode, in the same manner as mentioned above; thereby, an ammonia sensor of the present invention can be obtained.

In the ammonia sensor of this type, the ratio of the conductive high polymer matrix and the polyaniline in the ammonia-sensor material is not strictly restricted and can vary over a wide range depending upon the requirements for the ammonia sensor, its application, etc. However, the weight ratio of the polyaniline/the conductive high polymer can be generally 10/90 to 90/10, preferably 20/80 to 85/15, more preferably 30/70 to 80/20.

In the ammonia sensor provided by the present invention, the electric resistance of the polyaniline in the ammonia-sensing material changes in proportion of the concentration of ammonia gas, and the change is sharp even at room temperature and accordingly the sensing portion can function at room temperature. Further, the ammonia sensor of the present invention can be easily produced simply by, for example, coating an ammonia-sensing material on a substrate having electrodes thereon, as shown in FIG. 1, can be made small, thin and lightweight, causes no trouble such as separation from electrodes, and is easy to handle and maintain. Furthermore, the ammonia sensor of the present invention shows excellent linear change of electric resistance to the change of ammonia gas concentration, has a high sensitivity, and allows easy designing of electronic circuit containing it.

Thus, the ammonia sensor of the present invention can be used effectively for automation of ammonia concentration control, leakage detection, warning signal, and operation stop in various plants; detection of protein and amino acid by using in combination with an enzyme or microbe producing ammonia gas in the form of metabolism of protein or amino acid; and detection of ammonia gas generated in various reactions, or control of reaction based on the detection.

The present invention is described more specifically by way of Examples and the accompanying drawings.

BRIEF DESCRIPTION OF THE DRAWINGS

FIG. 1A is a plan view of the ammonia sensor.

FIG. 1B is a sectional view taken along line a—a shown in FIG. 1A.

FIG. 2-7 are graphs showing the electric resistance of the ammonia sensor and ammonia concentration according to the present invention.

DETAILED DESCRIPTION

Figure 4:
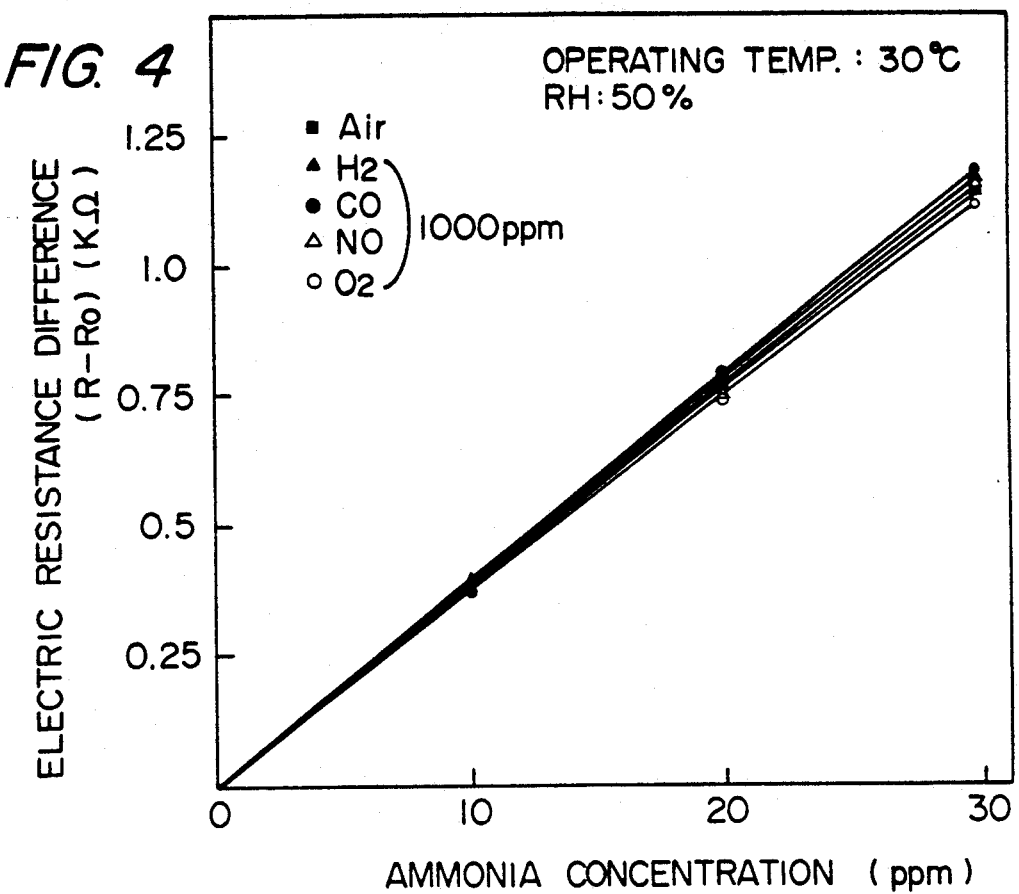

In the drawings, FIG. 1A and 1B are a schematic illustrations of an example of the ammonia sensor of the present invention, wherein the numeral 1 is a polyaniline membrane, the numeral 2 is an insulating substrate, the numeral 3 is interdigitated electrodes, and the numeral 4 is lead wires; FIGS. 2 to 7 are graphs each showing the relationship between the electric resistance of the ammonia sensor of the present invention and ammonia concentration.

EXAMPLE 1

40 g of ethanol, 30 g of propylene carbonate, 12 g of perchloric acid and 8 g of aniline were fed into an electrolytic cell (size=2 cm×2 cm), electrode-to-electrode distance=2 cm) wherein both the anode and the cathode are made of platinum. Then, electrolytic polymerization was effected for 10 minutes at a voltage of 0.7 V (relative to a standard calomel-alumel electrode), whereby a bluish black precipitate was formed. The precipitate was separated, washed with water until the pH of the washings became about 7, and vacuum dried at room temperature.

The resulting dry polyaniline was dissolved in N,N'-dimethylformamide to prepare a 10 weight % solution. The solution was spray coated on an alumina substrate having thereon a pair of interdigitated platinum electrodes (electrode width=100 $\mu$m, electrode-to-electrode distance=150 $\mu$m) as shown in FIG. 1, followed by drying to form a polyaniline film having a thickness of 10 $\mu$m.

The resulting ammonia sensor was set in a glass tube of 24 mm in diameter. Air was passed through the glass tube from its one end at a rate of 1 g/min; a given amount of ammonia was intermittently injected into the air current; and the electric resistance of the sensor was measured. The results of the measurement are shown in FIG. 2.

EXAMPLE 2

An ammonia sensor was produced according to the same procedure as in EXAMPLE 1 except that the propylene carbonate (30 g) used in EXAMPLE 1 was replaced by 10 g of water.

The ammonia sensor was set in a closed vessel; 10 ppm of ammonia gas was injected to the vessel at intervals of 4 minutes; and the electric resistance of the sensor was measured. The results of the measurement are shown in FIG. 3.

EXAMPLE 3

An ammonia sensor was produced in the same procedure as in EXAMPLE 1 except that the pechloric acid (12 g) was replaced by 15 g of tetraethylammonium fluoroborate, was propylene carbonate (30 g) was replaced by 10 g of water and the platinum cathode was replaced by a palladium cathode.

The ammonia sensor was set in a closed vessel; the vessel was filled with air alone or air containing 10,000 ppm of $H_2$, CO, NO or $O_2$; 10 ppm of ammonia was injected into the vessel at intervals of 4 minutes; the electric resistance of the sensor was measured; and there was prepared a graph showing the relationship between ammonia concentration (ppm) and electric resistance difference (R−R.). R is the measured value of electric resistance when ammonia was injected into air alone or air containing $H_2$, CO, NO or $O_2$; and R. is the measured value of electric resistance when only air was used and no ammonia was present. The results are shown in FIG. 4. As is clear from FIG. 4, the electric resistance of the ammonia sensor of the present invention is not affected by the co-presence of gas other than ammonia.

EXAMPLE 4

A solution consisting of 10 parts by weight of a polyaniline, 10 parts by weight of sodium thiocyanate and 80 parts by weight of N,N'-dimethylformamide was spin coated on a 96% alumina substrate (1 cm×1.5 cm) having thereon a-pair of interdegitated electrodes (electrode width=150 $\mu$m electrode-to-electrode distance=150 m) as shown in FIG. 1, followed by drying to form a thin film of a conductive high-molecular substrate having a thickness of 5 $\mu$m.

Then, electrolytic polymerization of aniline was effected in an electrolytic cell using the above-mentioned substrate having a thin film as an anode and a platinum plate as a cathode (electrode-to-electrode distance=2.0 cm), under the following conditions.

Composition of polymerization solution: 1.8 moles of acetonitrile, 1 mole of propylene carbonate, 0.5 mole of $HClO_4$ and 0.25 mole of aniline.

Voltage: 0.8 V (relative to a standard calomel-alumel electrode)

Current density: Constant current electrolysis at 20 mA/cm$^2$

Time: 10 minutes

After the completion of the electrolysis, the anode was taken out, washed with water until the pH of the washings became about 7, and dried at 50° C.

Figure 5:
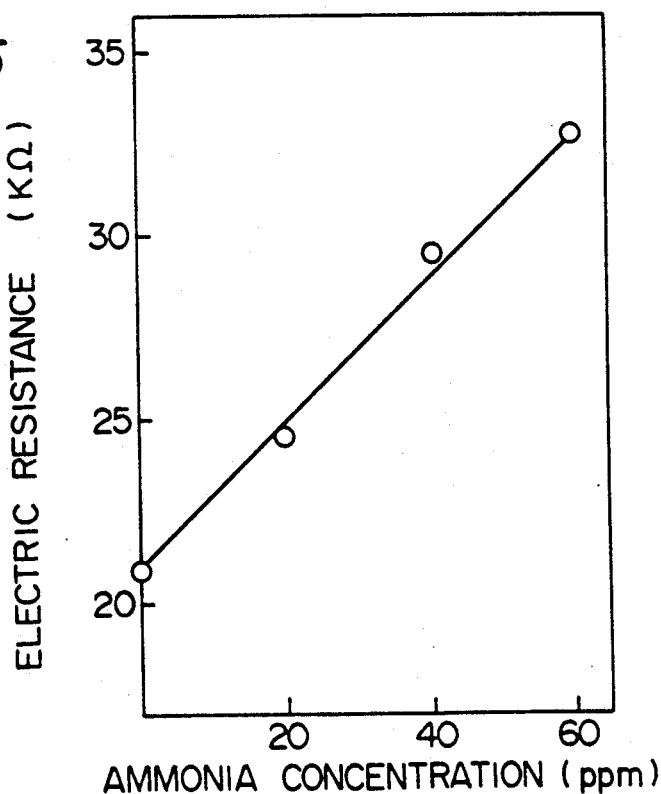

The resulting ammonia sensor was set in a glass tube having a diameter of 24 mm; air was passed through the tube from its one end at a rate of 1 l/min; a given amount of ammonia was intermittently injected into the air current; and the electric resistance of the sensor was measured. The results are shown in FIG. 5.

EXAMPLE 5

Figure 6:
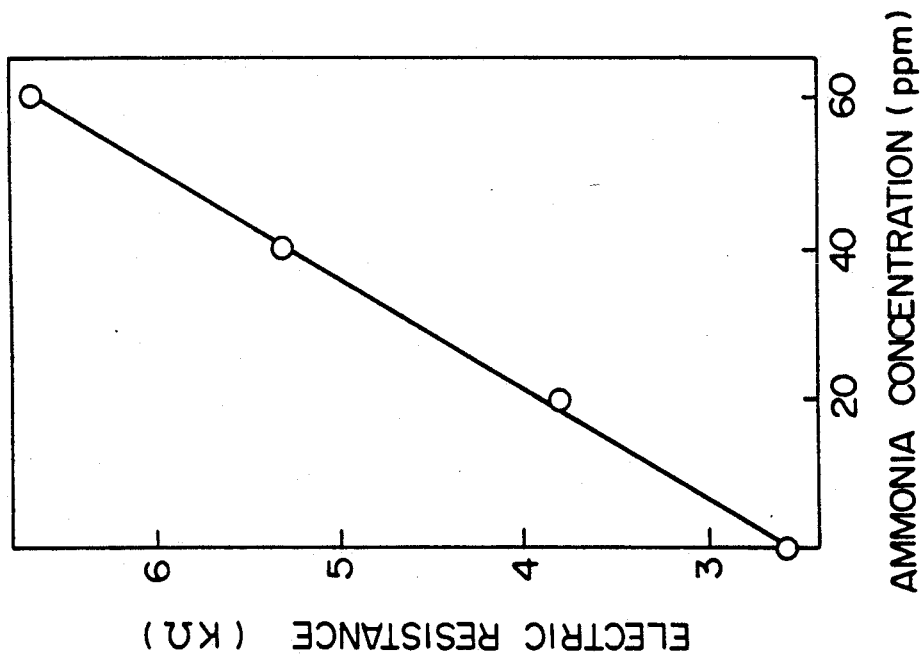

An ammonia sensor was produced in the same procedure as in EXAMPLE 4 except that the solution for forming a thin film of a conductive high polymer was changed to the following composition, i.e. a composition consisting of 7 parts by weight of a poly(ethylene oxide) (molecular weight=10,000), 3 parts by weight of lithium perchlorate and 90 parts by weight of water. The properties of the sensor were measured in the same manner as in EXAMPLE 4. The results are shown in FIG. 6.

EXAMPLE 6

An ammonia sensor was produced in the same procedure as in EXAMPLE 5 except that the acetonitrile (1.8 moles) used in the polymerization solution was changed to 2.0 moles of water. This ammonia sensor had about the same properties as the ammonia sensor produced in EXAMPLE 5.

EXAMPLE 7

Figure 7:
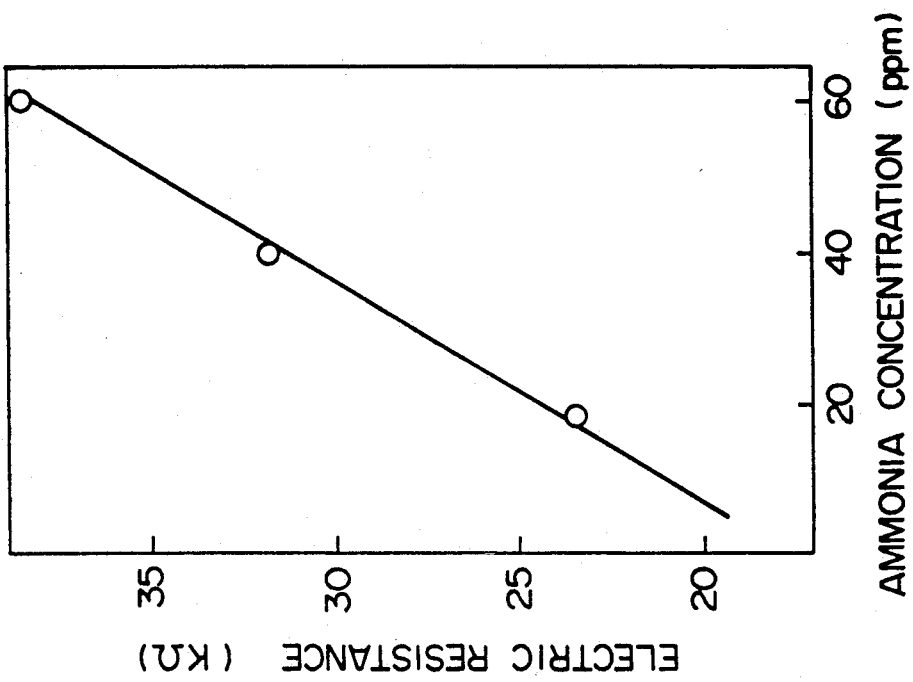

A solution consisting of 6 parts by weight of an acrylamide-methylpropanesulfonic acid copolymer, 2 parts by weight of a poly(vinyl alcohol) and 92 parts by weight of water was dip coated on the same alumina substrate having a pair of electrodes thereon, as used in EXAMPLE 4, followed by drying at 130° C. to form a think film of a conductive high polymer having a thickness of 10 $\mu$m. A Using this substrate having a thin film, as an anode, electrolytic polymerization was effected in the same manner as in EXAMPLE 4 to obtain an ammonia sensor. The properties of this ammonia sensor were measured in the same manner as in EXAMPLE 4. The results are shown in FIG. 7.

What we claim is:

1. An ammonia sensor consisting of at least one pair of electrodes and an ammonia-sensing material filling the space between the electrodes wherein the ammonia-sensing material comprises a matrix of a conductive polymer having a conductivity of $10^{-5}$ mho or higher and a polyaniline dispersed in the matrix.

2. An ammonia sensor according to claim 1, wherein the polyaniline is produced by electrolytic polymerization of aniline.

3. An ammonia sensor according to claim 1, wherein the electrodes are provided on an insulating substrate and are an interdigitated form.

4. An ammonia sensor according to claim 1, which is produced by coating a polyaniline solution on an insulating substrate having at least one pair of electrodes thereon, so as to fill at least the space between the electrodes.

5. An ammonia sensor according to claim 1, wherein the conductive polymer is selected from high-molecular electrolytes, their crosslinked products and mixtures of a polymer and an electrolyte.

6. An ammonia sensor according to claim 1, wherein the weight ratio of the polyaniline to the conductive polymer is 10/90 to 90/10.

7. An ammonia sensor according to claim 1, which is produced by forming a film having a thickness of 0.1 to 100 microns of a conductive polymer on an insulating substrate having at least one pair of electrodes thereon and then effecting electrolytic polymerization of aniline with said film of conductive polymer used as an anode.

8. An ammonia sensor consisting of at least one pair of electrodes and an ammonia sensing material comprising a film matrix of a conductive polymer having a conductivity of $10^{-5}$ mho or higher and a polyaniline dispersed in the matrix, wherein the weight ratio of the polyaniline to the conductive polymer is 10/90 to 90/10.

9. An ammonia sensor according to claim 8, wherein the electrodes are provided on an insulating substrate and are an interdigitated form.

10. An ammonia sensor according to claim 8 wherein the film matrix has a thickness of 1 to 20 microns.

11. An ammonia sensor according to claim 8 wherein the weight ratio of polyaniline to the conductive polymer is 20/80 to 85/15.

12. A process for detecting the ammonia concentration of a gas containing ammonia which comprises contacting the ammonia sensor of claim 1 with an ammonia containing gas, measuring an electric resistance change of the ammonia-sensing material, and determining the concentration of ammonia from said change of electric resistance of the sensing material.

13. A process for detecting the ammonia concentration of a gas containing ammonia which comprises contacting the ammonia sensor of claim 8 with an ammonia containing gas, measuring an electric resistance change of the ammonia-sensing material, and determining the concentration of ammonia from said change of electric resistance of the sensing material.

* * * * *